US011733775B2

(12) United States Patent
An et al.

(10) Patent No.: US 11,733,775 B2
(45) Date of Patent: Aug. 22, 2023

(54) CONVENIENT DEVICE CONTROL APPARATUS FOR VEHICLE AND METHOD THEREOF

(71) Applicants: Hyundai Motor Company, Seoul (KR); Kia Motors Corporation, Seoul (KR)

(72) Inventors: Dae Yun An, Gyeonggi-do (KR); Eung Hwan Kim, Seoul (KR); Gyun Ha Kim, Incheon (KR); Seul Ki Jeon, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 890 days.

(21) Appl. No.: 16/554,086

(22) Filed: Aug. 28, 2019

(65) Prior Publication Data
US 2020/0356170 A1    Nov. 12, 2020

(30) Foreign Application Priority Data
May 8, 2019    (KR) .................. 10-2019-0053490

(51) Int. Cl.
*G06F 3/00* (2006.01)
*G06F 3/01* (2006.01)
*B60W 10/30* (2006.01)
*B60K 35/00* (2006.01)
*A61B 5/18* (2006.01)
*A61B 5/374* (2021.01)

(52) U.S. Cl.
CPC .............. *G06F 3/015* (2013.01); *A61B 5/18* (2013.01); *A61B 5/374* (2021.01); *B60K 35/00* (2013.01); *B60W 10/30* (2013.01); *B60K 2370/152* (2019.05); *B60K 2370/347* (2019.05)

(58) Field of Classification Search
CPC ........................... G06F 3/015; B60R 16/0231
See application file for complete search history.

(56) References Cited

U.S. PATENT DOCUMENTS

| 7,123,955 | B1 * | 10/2006 | Gao ....................... A61B 5/377 340/4.13 |
| 7,127,283 | B2 * | 10/2006 | Kageyama .......... B60R 16/0231 600/545 |
| 10,310,600 | B2 | 6/2019 | Hong et al. |
| 11,027,669 | B1 * | 6/2021 | Kato ....................... B60R 11/04 |

(Continued)

FOREIGN PATENT DOCUMENTS

KR    101648017 B1    8/2016

OTHER PUBLICATIONS

Chen, Xiaogang, et al. "High-speed spelling with a noninvasive brain-computer interface." Proceedings of the national academy of sciences 112.44 (2015): E6058 E6067, p. 1-10.

*Primary Examiner* — Qutbuddin Ghulamali
(74) *Attorney, Agent, or Firm* — Fox Rothschild LLP

(57) ABSTRACT

A convenient device control apparatus for a vehicle and a method thereof are provided. The convenient device control apparatus includes a light source that emits light at a specified frequency and an electroencephalogram (EEG) sensor that measures an EEG signal of a user. An EEG analyzer analyzes a frequency of the EEG signal measured by the EEG sensor and a controller operates a convenient device in the vehicle based on the frequency of the EEG signal analyzed by the EEG analyzer.

20 Claims, 8 Drawing Sheets

(56) References Cited

U.S. PATENT DOCUMENTS

| | | | |
|---|---|---|---|
| 2009/0187114 A1* | 7/2009 | Morikawa | G06F 3/015 600/545 |
| 2010/0010365 A1* | 1/2010 | Terao | B60K 28/063 600/544 |
| 2012/0220889 A1* | 8/2012 | Sullivan | A61B 5/378 600/544 |
| 2016/0282940 A1* | 9/2016 | Hong | B60K 35/00 |
| 2017/0349098 A1* | 12/2017 | Uhm | G08G 1/0967 |

\* cited by examiner

CONVENIENT DEVICE CONTROL APPARATUS FOR VEHICLE AND METHOD THEREOF

CROSS-REFERENCE TO RELATED APPLICATION

This application claims the benefit of priority to Korean Patent Application No. 10-2019-0053490, filed on May 8, 2019, the entire contents of which are incorporated herein by reference.

TECHNICAL FIELD

The present disclosure relates to a technique for providing convenience to a user in connection with operation of various convenient devices mounted on a vehicle, and more particular, to a convenient device control apparatus that allows a user to operate various convenient devices mounted on the vehicle by grasping a user's intention to operate the convenient devices based on an EEG signal of the user and controlling the convenient devices corresponding to the intention of the user.

BACKGROUND

Recently, a vehicle has been developed with various convenient devices, such as a power window, an electric seat, an electric footrest, an electric sunshade, a lighting device, an air conditioner, a display, an entertainment device, and the like, for providing various convenient functions in addition to various safety devices. Such various convenient devices are generally operated by user engagement of a button. However, in consideration of the inconvenience of a user, there has been proposed a technique that controls a corresponding convenient device by recognizing the gesture or speech of a user.

Such conventional techniques also require the user to make a gesture for operating the convenience device or command the operation by voice, and thus, the convenience of a user may be deteriorated. In particular, a user who is seated in the back seat of a vehicle may often operate the seat in a rest mode (e.g., a state in which the backrest is laid down and the front seat is used as a footrest), and thus it may be difficult to operate the convenience device since the distance from the device for recognizing the user's gesture or the device for recognizing the user's voice is substantial.

SUMMARY

The present disclosure provides a convenient device control apparatus for a vehicle which is capable of allowing a user to easily operate various convenient devices mounted on the vehicle by grasping a user's intention to operate the convenient devices based on an electroencephalogram (EEG) signal of the user and operating the convenient devices based on the intention of the user, and a method thereof.

The technical problems to be solved by the present inventive concept are not limited to the aforementioned problems, and any other technical problems not mentioned herein will be clearly understood from the following description by those skilled in the art to which the present disclosure pertains.

According to an aspect of the present disclosure, a convenient device control apparatus for a vehicle may include a light source configured to emit light at a specified frequency, an electroencephalogram (EEG) sensor configured to measure an EEG signal of a user, an EEG analyzer configured to analyze a frequency of the EEG signal measured by the EEG sensor, and a controller configured to operate a convenient device in the vehicle based on the frequency of the EEG signal analyzed by the EEG analyzer.

The controller may be configured to change a light emission frequency of the light source corresponding to an operation state of the convenient device. Additionally, the controller may be configured to change a light emission color of the light source that corresponds to a light emission frequency of the light source. The controller may be configured to allow the light source to emit light a specified number of times by a time interval at a time point when operating the convenient device. The controller may be configured to increase a light emission intensity of the light source at a time point when operating the convenient device. The controller may also be configured to change a light emission color of the light source at a time point when operating the convenient device. The light source may be located around the convenient device.

According to another aspect of the present disclosure, a method of controlling a convenient device of a vehicle may include emitting, by a light source, light at a specified frequency, measuring, by an electroencephalogram (EEG) sensor, an EEG signal of a user, analyzing, by an EEG analyzer, a frequency of the EEG signal measured by the EEG sensor, and operating, by a controller, a convenient device in the vehicle based on the frequency of the EEG signal analyzed by the EEG analyzer.

The operation of the convenient device in the vehicle may include changing the light emission frequency of the light source that corresponds to an operation state of the convenient device. In addition, the operation of the convenient device in the vehicle may include changing a light emission color of the light source that corresponds to a light emission frequency of the light source and allowing the light source to emit light a specified number of times by a time interval at a time point when operating the convenient device. The operation of the convenient device in the vehicle may also include increasing a light emission intensity of the light source at a time point when operating the convenient device. In addition, the operation of the convenient device in the vehicle may include changing a light emission color of the light source at a time point when operating the convenient device. The light source may be located around the convenient device.

According to still another aspect of the present disclosure, a convenient device control apparatus for a vehicle may include a plurality of light sources having light emission frequencies different from each other, an electroencephalogram (EEG) sensor configured to measure an EEG signal of a user, an EEG analyzer configured to analyze a frequency of the EEG signal measured by the EEG sensor, and a controller configured to operate a convenient device in the vehicle based on the frequency of the EEG signal analyzed by the EEG analyzer.

The controller may be configured to operate the convenient device when an EEG signal having a first frequency and an EEG signal having a second frequency are successively measured within a specified time. The controller may be configured to change a light emission color of the light source that corresponds to the light emission frequency of the light source. Additionally, the controller may be configured to allow the light source to emit light a specified number of times by a time interval at a time point when operating the convenient device. The controller may be configured to increase a light emission intensity of the light source at a time point when operating the convenient device. The controller may be configured to change a light emission color of the light source at a time point when operating the convenient device.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
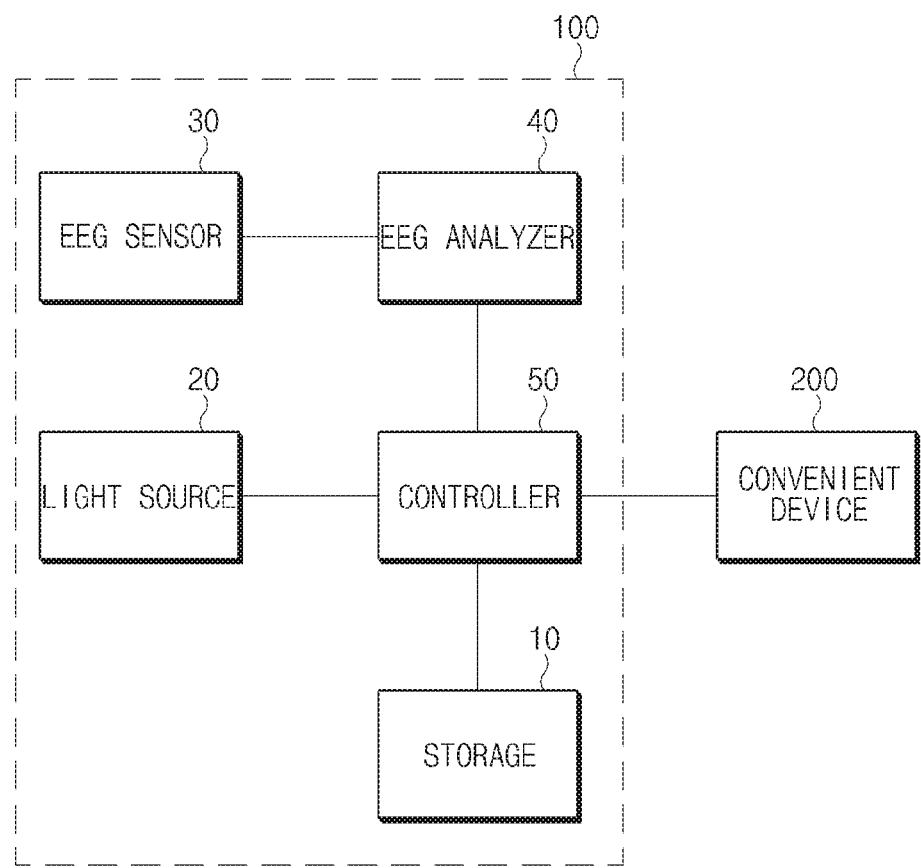
FIG. 1 is a block diagram illustrating a configuration of a convenient device control apparatus for a vehicle according to an exemplary embodiment of the present disclosure.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, some exemplary embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the exemplary embodiment of the present disclosure, a detailed description of well-known features or functions will be ruled out in order not to unnecessarily obscure the gist of the present disclosure.

In describing the components of the exemplary embodiment according to the present disclosure, terms such as first, second, "A", "B", (a), (b), and the like may be used. These terms are merely intended to distinguish one component from another component, and the terms do not limit the nature, sequence or order of the constituent components. Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

FIG. 1 is a block diagram illustrating a configuration of a convenient device control apparatus for a vehicle according to an exemplary embodiment of the present disclosure. As shown in FIG. 1, a convenient device control apparatus 100 for a vehicle according to an exemplary embodiment of the present disclosure may include storage 10, a light source 20, an electroencephalogram (EEG) sensor 30, an EEG analyzer 40, and a controller 50. Meanwhile, according to a manner of implementing the convenient device control apparatus 100 for a vehicle according to an exemplary embodiment of the present disclosure, components may be coupled to each other to form one unit. In addition, some of the components may be omitted depending on a manner of carrying out an exemplary embodiment.

Referring to each component, the storage 10 may be configured to obtain the intention of a user of operating various convenient devices in the vehicle based on an EEG signal of the user, and may be configured to store various logics, algorithms, and programs required in operating the convenient devices corresponding to the obtained intention of the user. The storage 10 may be configured to store various data set by the user. For example, the storage 10 may be configured to store functions such as turning on of an indoor light as a function matched to a first EEG signal, turning off of the indoor light as a function matched to a second EEG signal, a sunshade raise as a function matched to a third EEG signal, a sunshade down as a function matched to a fourth EEG signal, window opening as a function matched to a fifth EEG signal, window closing as a function matched to a sixth EEG signal, turning on of an entertainment device as a function matched to a seventh EEG signal, and turning off of the entertainment device as a function matched to an eighth EEG signal.

In addition, the storage 10 may further be configured to store EEG signals related to functions of a room lamp, a display, an audio video navigation (AVN) system, a door lock/unlock, a rear seat entertainment monitor, a seat heating wire, a ventilation seat, a steering wheel heating wire, and the like. The storage 10 may include at least one type of a storage medium of memories of a flash memory type, a hard disk type, a micro type, a card type (e.g., a secure digital (SD) card or an extreme digital (XD) card), and the like, and a random access memory (RAM), a static RAM (SRAM), a read-only memory (ROM), a programmable ROM (PROM), an electrically erasable PROM (EEPROM), a magnetic memory (MRAM), a magnetic disk, and an optical disk type memory.

Further, the light source 20 may be implemented with a light-emitting diode (LED), and may be mounted in the interior of the vehicle to be used to operate various convenient devices. The light source 20 may be configured to emit light at a frequency that corresponds to each EEG signal matched with the functions of various convenient devices mounted on the vehicle under operation of the controller 50. The light of the light source 20 emitting light at a specific frequency may be configured to perform a function of a visual stimulus signal.

For example, the light source 20 may be configured to emit light (a first light emission frequency) at a first frequency that corresponds to the first EEG signal, light (a second light emission frequency) at a second frequency that corresponds to the second EEG signal, light (a third light emission frequency) at a third frequency that corresponds to the third EEG signal, light (a fourth light emission frequency) at fourth frequency that corresponds to the fourth EEG signal, light (a fifth light emission frequency) at a fifth frequency that corresponds to the fifth EEG signal, light (a sixth light emission frequency) at a sixth frequency that corresponds to the sixth EEG signal, light (a seventh light emission frequency) at a seventh frequency that corresponds to the seventh EEG signal, and light (an eighth light emission frequency) at an eighth frequency that corresponds to the eighth EEG signal.

The EEG sensor 30, which is a type of sensor mounted on a headrest of a seat, may be configured to measure the EEG signal of a user in a contact or non-contact manner. The EEG sensor 30 may include a plurality of EEG electrodes that make contact with a scalp, which are divided into a signal electrode and a reference electrode. When the EEG electrodes are in contact with the occipital lobe, a flow of electricity generated when a signal is transmitted between neurons in the nervous system may be measured through the EEG electrodes.

The EEG sensor 30 may be configured to measure the EEG signal based on the steady-state visual evoked potential (SSVEP) principle. In other words, the EEG sensor 30 may be configured to measure the EEG signal using the principle that a frequency pattern of the same frequency band as that of a specific frequency occurs in the occipital lobe when a human stares at a visual stimulation signal having the specific frequency. For reference, the EEG refers to a potential obtained by measuring, through an electrode, a signal of a fine brain surface generated by synthesizing electrical signals generated from numerous nerves of the brain. The SSVEP is an EEG signal induced near the occipital lobe that is responsible for the visual field when staring at a visual stimulation signal provided at a particular frequency. Since the SSVEP includes a frequency component equal to the frequency of the visual stimulation signal, the frequency of the EEG signal measured at the occipital lobe of the user may be compared with that of the visual stimulation signal provided to the user to determine whether the user stares at the corresponding visual stimulation signal.

Figure 2:
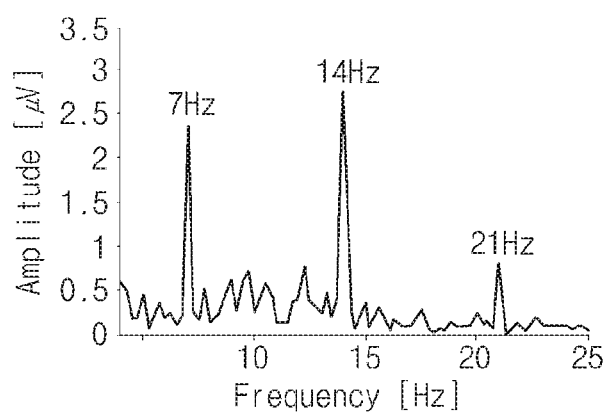
FIG. 2 is a view illustrating a light emission frequency of a light source included in a convenient device control apparatus for a vehicle and SSVEP corresponding thereto according to an exemplary embodiment of the present disclosure.

FIG. 2 is a view illustrating a light emission frequency of a light source included in a convenient device control apparatus for a vehicle and SSVEP corresponding thereto according to an exemplary embodiment of the present disclosure. When the light source 20 mounted in the vehicle emits light at a frequency of about 7 Hz, as shown in FIG. 2, the EEG sensor 30 may be configured to measure EEG signals of a frequency of 7 Hz and its harmonics at the occipital lobe of a user.

Meanwhile, the EEG sensor 30 may further include a transmitter (not shown) configured to wirelessly transmit the measured EEG signal to the EEG analyzer 40 or an external server. In particular, the transmitted EEG signal may be an analog signal or a digital signal. When a digitally converted EEG signal is transmitted, the transmitter may include an analog-to-digital converter (ADC). In addition, the transmitter may include at least one of a mobile communication module, a wireless Internet module, and a short-range communication module.

The mobile communication module may be configured to transmit an EEG signal in a mobile communication network in technical standards or communication schemes for mobile communication (e.g., global system for mobile communication (GSM), code division multi access (CDMA), CDMA 2000, enhanced voice-data optimized or enhanced voice-data only (EV-DO), wideband CDMA (WCDMA), high speed downlink packet access (HSDPA), high speed uplink packet access (HSUPA), long term evolution (LTE), long term evolution-advanced (LTEA), and the like).

The wireless Internet module, which is a module for wireless Internet access, may be configured to transmit an EEG signal through wireless LAN (WLAN), a wireless fidelity (Wi-Fi), a wireless fidelity (Wi-Fi) direct, digital living network alliance (DLNA), wireless broadband (Wi-Bro), world interoperability for microwave access (WiMAX), high speed downlink packet access (HSDPA), high speed uplink packet access (HSUPA), long term evolution (LTE), long term evolution-advanced (LTE-A), and the like. The short-range communication module may support short range communication by using at least one of technologies of Bluetooth™, radio frequency identification (RFID), Infrared Data Association (IrDA), Ultra Wide Band (UWB), ZigBee, Near Field Communication (NFC) and Wireless Universal Serial Bus (USB) technologies.

Furthermore, the EEG analyzer 40 may be configured to determine whether the EEG signal of a user measured by the EEG sensor 30 has a specific frequency. In particular, the EEG analyzer 40 may use various types of analysis techniques. For example, a power spectral density analysis technique and a canonical correlation analysis technique may be used.

The EEG analyzer 40 may be configured to perform a preprocessing process such as amplification or filtering before analyzing the EEG signal. The EEG analyzer 40 may use a frequency band filter such as a high-pass filter to pass only frequencies in a specific band or use a spatial filter to remove or emphasize a spatial frequency band. For example, a frequency signal below about 0.1 Hz may be blocked using a high-pass filter, or a low weight may be allocated to the peripheral signal of the motor cortex and the EEG of the motor cortex to be measured may be amplified.

As the spatial filter, a filter such as a common average reference (CAR), a large surface laplacian (Large SL), a small surface laplacian (Small SL), a common spatial pattern (CSP), and the like may be used, and it may be possible to remove noise of an EEG signal using a noise removal algorithm such as independent component analysis (ICA), linear discriminant analysis (LDA), principal component analysis (PCA), canonical correlation analysis (CCA), and the like.

The EEG analyzer 40 may be configured to analyze a frequency component of an EEG signal. For example, a frequency-sequence power spectrum may be obtained through a Fourier transform, and a specific frequency component may be determined by comparing magnitudes of power spectrum values. Since the EEG signal of the user staring at the visual stimulation signal may include a fundamental frequency, which is a frequency of the visual stimulation signal, and harmonic frequencies which are multiples of the fundamental frequency, the EEG analyzer 40 may be configured to determine the frequency component of the EEG signal through Cepstrum analysis.

In the exemplary embodiment of the present disclosure, although an example in which the EEG analyzer 40 is implemented in a separate configuration has been described, the EEG analyzer 40 may be integrated into the controller 50 and the controller 50 may be configured to execute the functions of the EEG analyzer 40 in a batch. Next, the controller 50 may be configured to execute overall control such that each of the components performs a respective function normally. The controller 50 may be implemented in the form of hardware or software, or a combination of hardware and software. The controller 50 may be implemented with a microprocessor, but the exemplary embodiment is not limited thereto.

Additionally, the controller 50 may be configured to obtain the intention of the user to manipulate various convenient devices in the vehicle based on the EEG signal of the user, and perform various controls required in the process of operating the corresponding convenient devices corresponding to the obtained intention of the user.

First Embodiment

In the first exemplary embodiment, a method of controlling various functions of one convenient device 200 using one light source 20 is provided, where the controller 50 may be configured to change the light emission frequency of the light source 20 that corresponds to a situation and thus, various functions of the convenient device 200 may be executed by the one light source 20.

Figure 3:
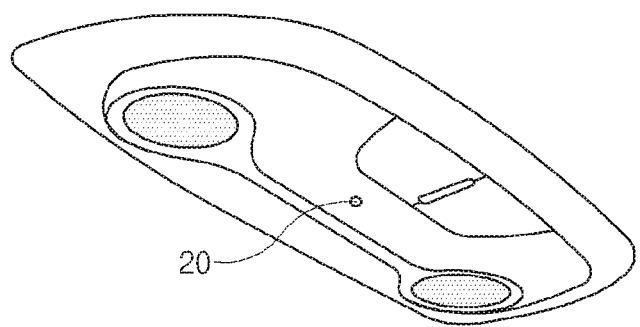
FIG. 3 is a view illustrating a light source provided in a convenient device control apparatus for a vehicle according to a first exemplary embodiment of the present disclosure.

Hereinafter, the detailed description will be given with reference to FIG. 3. FIG. 3 is a view illustrating a light source provided in a convenient device control apparatus for a vehicle according to a first exemplary embodiment of the present disclosure. As one example of the convenient device, an indoor light will be described.

As shown in FIG. 3, when the interior light is in an off state, the controller 50 may be configured to set the light emission frequency of the light source 20 to a first frequency (e.g., about 40 Hz) such that the user turns on the interior light. Thereafter, when the user stares at the light source 20, the controller 50 may be configured to obtain a first frequency pattern using the EEG sensor 30 and the EEG analyzer 40 and perform a function of turning on the interior light that corresponds to the first frequency. Then, the controller 50 may be configured to set the emission frequency of the light source 20 to a second frequency (e.g., about 50 Hz) so that the user may turn off the interior light when the interior light is on.

In particular, to improve the awareness of the user for each function, for example, the controller 50 may be configured to set the light emission color of the light source 20 to red when the emission frequency of the light source 20 is set to the first frequency (e.g., the light source 20 may emit light at the first frequency), and the controller 50 may be configured to set the light emission color of the light source 20 to blue when the emission frequency of the light source 20 is set to the second frequency (e.g., the light source 20 may emit light at the second frequency). In addition, when the first or second frequency pattern is obtained, to inform the user of the pattern, the controller 50 may be configured to operate the light source 20 to emit light a specified number of times by a time interval, increase the light emission intensity of the light source 20, or change the light emission color (e.g., green) of the light source 20. In particular, the light source 20 may be disposed around the interior light, but is not limited thereto.

Meanwhile, the controller 50 may implement a setting mode by providing an additional light source around the interior lighting. For example, when the light source 20 for operating the interior lamp and an additional light source are provided, the user may enter a setting mode by staring at the additional light source. In particular, the controller 50 may be configured to repeatedly turn the additional light source on and off to notify the user that the setting mode is activated. Of course, both the light source 20 and the additional light source may be repeatedly turned on and off (e.g., blinking pattern).

When the user directly operates the window in the setting mode, the controller 50 may be configured to stop blinking of the additional light source and enter a light source setting process. In other words, the controller 50 may be configured to determine the order of the light sources at which the user stares. Through such a process, the controller 50 may be configured to set the function of another convenient device using the light source of the interior light through the staring order of the light source 20 and the additional light source. When there are a plurality of additional light sources, one function may be set to one light source without using a combination thereof. The first exemplary embodiment may further include a display operated by the controller 50 to display the current operation mode of a convenient device as a phrase or an icon to improve the user's awareness of the operation of the convenient device.

Second Embodiment

In the second exemplary embodiment, a method of controlling various functions of one convenient device 200 using the plurality of light sources 20 is provided, where each light source 20 is matched with each function of the convenient device 200.

Figure 4:
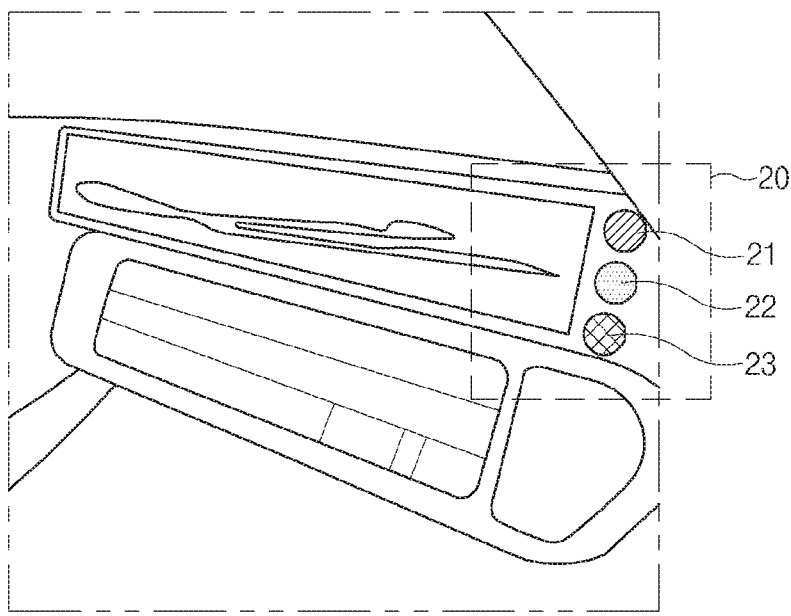
FIG. 4 is a view illustrating a light source provided in a convenient device control apparatus for a vehicle according to a second exemplary embodiment of the present disclosure.

Hereinafter, the detailed description will be given with reference to FIG. 4. FIG. 4 is a view illustrating a light source provided in a convenient device control apparatus for a vehicle according to a second exemplary embodiment of the present disclosure. As one example of the convenient device, an AVN system will be described.

As shown in FIG. 4, a plurality of light sources 20 may be provided, where a first light source 21 may emit light at a frequency (e.g., about 40 Hz) for turning on the audio video navigation (AVN) system under operation of the controller 50. As one example, the light emission color may be red. A second light source 22 may emit light at a frequency (e.g., about 50 Hz) for turning off the AVN system under operation of the controller 50, and as one example, the light emission color may be blue. A third light source 23 may emit light at a frequency (e.g., about 60 Hz) for entering a channel changing mode under operation of the controller 50, and as one example, the light emission color may be purple.

The first exemplary embodiment may be added to the second exemplary embodiment. In other words, when entering the channel changing mode, the controller 50 may be configured to operate the first light source 21 to emit light at a frequency for raising the channel, operate the second light source 22 to emit light at a frequency for lowering the channel, and operate the third light source 23 to emit light at a frequency for leaving the channel changing mode. During this process, the controller 50 may be configured to recognize the light emissions as another function based on the situation without changing the light emission frequency of each light source.

For example, when entering the channel changing mode, the frequency for turning on the AVN system may be recognized as a frequency for raising the channel, the frequency for turning off the AVN system as the frequency for lowering the channel, and the frequency for entering the channel changing mode as the frequency for leaving the channel changing mode.

Figure 5:
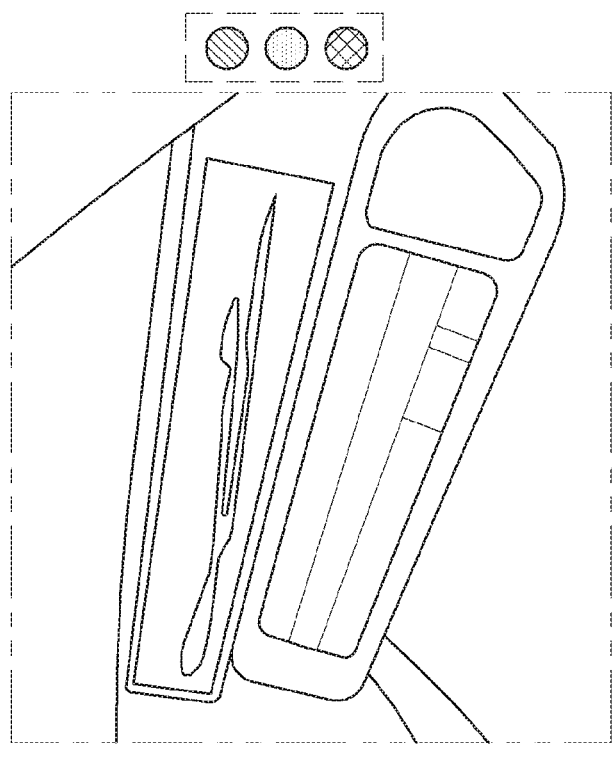
FIG. 5 is a view illustrating a light emission color of each light source in the second embodiment of the light source provided in the convenient device control apparatus for a vehicle according to an exemplary embodiment of the present disclosure.
Figure 5:
Figure 5:
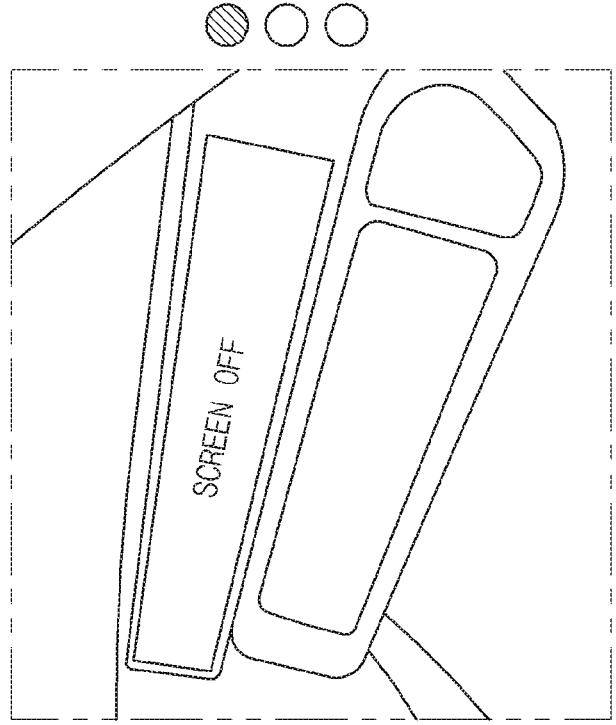

FIG. 5 is a view illustrating a light emission color of each light source in the second exemplary embodiment of the light source provided in the convenient device control apparatus for a vehicle according to an exemplary embodiment of the present disclosure. As shown in FIG. 5, when the AVN system is in the off state, the controller 50 may be configured to operate the first light source 21 to emit red light for turning on the AVN system and may be configured to turn off the remaining second and third light sources 22 and 23.

Thereafter, when the AVN system is turned on, the controller 50 may be configured to turn on all the light sources 20. When the AVN system is turned on, the controller 50 may be configured to display the current operation mode of the AVN system as a phrase or icon on the display to improve the awareness of the user for each function. The controller 50 may also be configured to set the function of each light source from the user through the input device of the AVN system.

Third Embodiment

The third exemplary embodiment is a method of operating convenient devices through a combination of the plurality of light sources, which may be applied to the combination of the first and second exemplary embodiments or the second exemplary embodiment. In particular, the controller 50 may be configured to execute the functions of various convenient devices in the vehicle through the combination of EEG signals having different frequencies analyzed by the EEG analyzer 40.

For example, when the first light source 21 emitting light at the first frequency and the second light source 22 emitting light at the second frequency are provided for operating the sunshade, the controller 50 may be configured to raise the sunshade when the first EEG signal that corresponds to the first frequency of the first light source 21 and the second EEG signal that corresponds to the second frequency of the second light source 22 are successively measured within a critical time period. When the second EEG signal that corresponds to the second frequency of the second light source 22 and the first EEG signal that corresponds to the first frequency of the first light source 21 are sequentially measured within the critical time period, the controller 50 may be configured to lower the sunshade Particularly, in the operation of raising the sun shade, the user knows in advance that the first light source 21 emitting light at the first frequency should be stared at for a certain period of time (e.g., 1 to 1.5 seconds) and then the second light source 22 emitting at the second frequency should be stared at for a certain period of time (e.g., 1 to 1.5 seconds). In addition, to lower the sunshade, the user knows in advance that the second light source 22 emitting light at the second frequency should be stared at for a certain period of time (e.g., 1 to 1.5 seconds) and then the first light source 21 emitting light at the first frequency should be stared at for a certain period of time (e.g., 1 to 1.5 seconds).

The controller 50 may be configured to obtain or detect intention of the user to operate a power window, operate an electric sunshade, adjust an electric seat angle, operate an electric footrest, operate a lighting device, operate an air conditioner, operate a display, operate an entertainment device, and the like, through a combination of EEG signals having different frequencies, and then may perform the corresponding operation. The controller 50 may be configured to set the light emission color of the first light source 21 to, for example, red and the light emission color of the second light source 22 to, for example, blue to raise the awareness of the user for each function.

When the first EEG signal that corresponds to the first frequency of the first light source 21 and the second EEG signal that corresponds to the second frequency of the second light source 22 are sequentially measured within a critical period of time, or when the second EEG signal that corresponds to the second frequency of the second light source 22 and the first EEG signal that corresponds to the first frequency of the first light source 21 are sequentially measured within a critical period of time, to provide a notification to the user, the controller 50 may be configured to operate the light source 20 to emit light a specified number of times by a time interval, increase the light emission intensity of the light source 20, or change the light emission color of the light source 20 (e.g., into green). In other words, the controller 50 may be configured to operate the light source 20 to emit light a specified number of times by a time interval, increase, increase the light emission intensity of the light source 20, or change the light emission color of the light source 20 (e.g., green).

According to the third exemplary embodiment, a display device may be further included to display the current operation mode of the convenient device on the display as a phrase or an icon to raise the awareness of the user for the operation of the convenient device.

Figure 6:
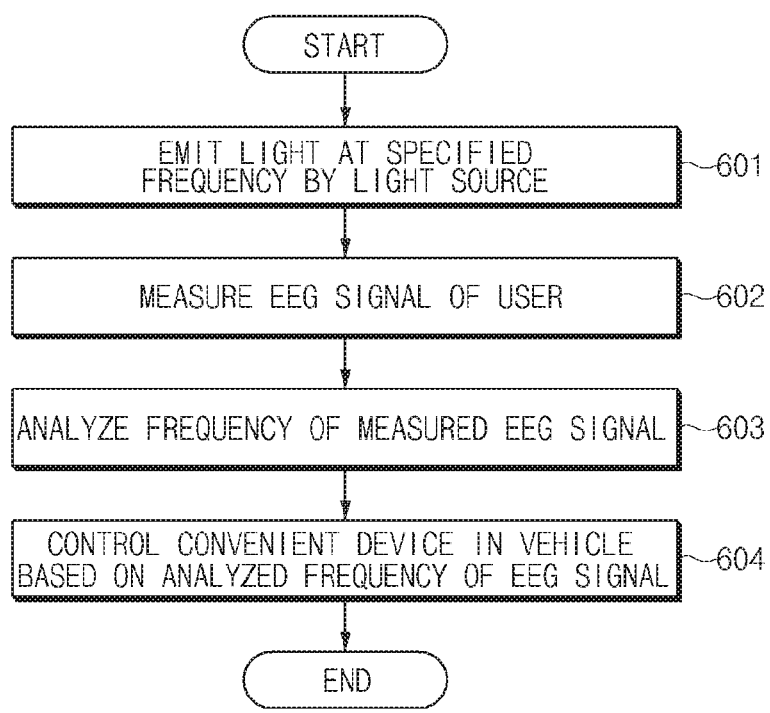
FIG. 6 is a flowchart illustrating a method of operating a convenient device of a vehicle according to an exemplary embodiment of the present disclosure.

FIG. 6 is a flowchart illustrating a method of operating a convenient device of a vehicle according to an exemplary embodiment of the present disclosure. First, the light source 20 may be configured to emit light at a specified frequency in operation 601. Then, the EEG sensor 30 may be configured to measure an EEG signal of a user in operation 602. The EEG analyzer 40 may be configured to analyze the frequency of the EEG signal measured by the EEG sensor 30 in operation 603. In other words, the EEG analyzer 40 may be configured to detect an EEG signal has a specific frequency. Thereafter, the controller 50 may be configured to operate the convenient device in the vehicle based on the frequency of the EEG signal analyzed by the EEG analyzer 40 in operation 604.

Figure 7:
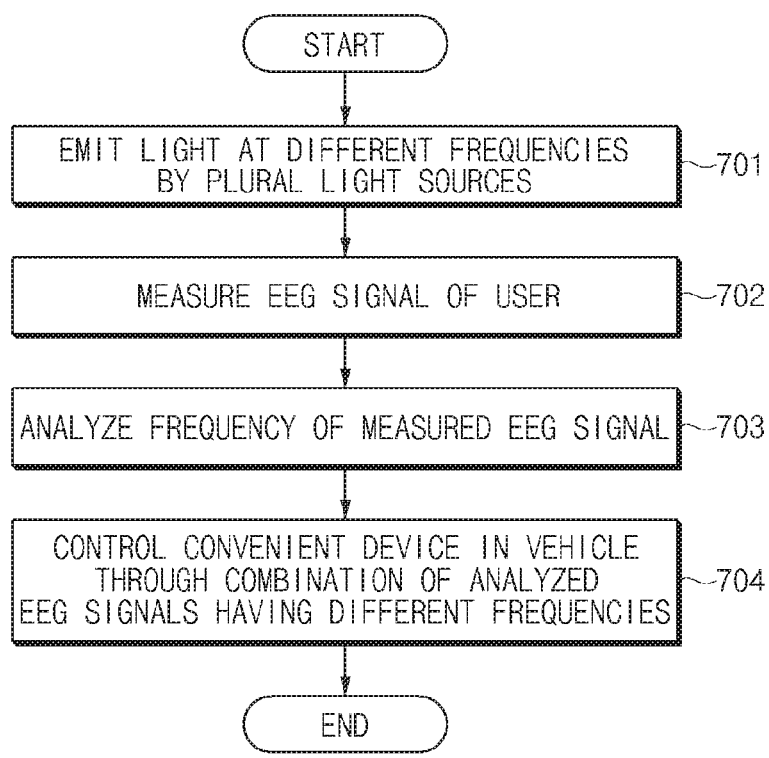
FIG. 7 is a flowchart illustrating a method of operating a convenient device of a vehicle according to another exemplary embodiment of the present disclosure.

FIG. 7 is a flowchart illustrating a method of operating a convenient device of a vehicle according to another exemplary embodiment of the present disclosure. First, a plurality of light sources emit light at different frequencies in operation 701. Then, the EEG sensor 30 may be configured to emit an EEG signal of a user in operation 702. The EEG analyzer 40 may be configured to analyze the frequency of the EEG signal measured by the EEG sensor 30 in operation 703. In other words, the EEG analyzer 40 may be configured to detect an EEG signal has a specific frequency. Thereafter, the controller 50 may be configured to operate a convenient device in the vehicle through a combination of EEG signals having different frequencies analyzed by the EEG analyzer 40 in operation 704.

Figure 8:
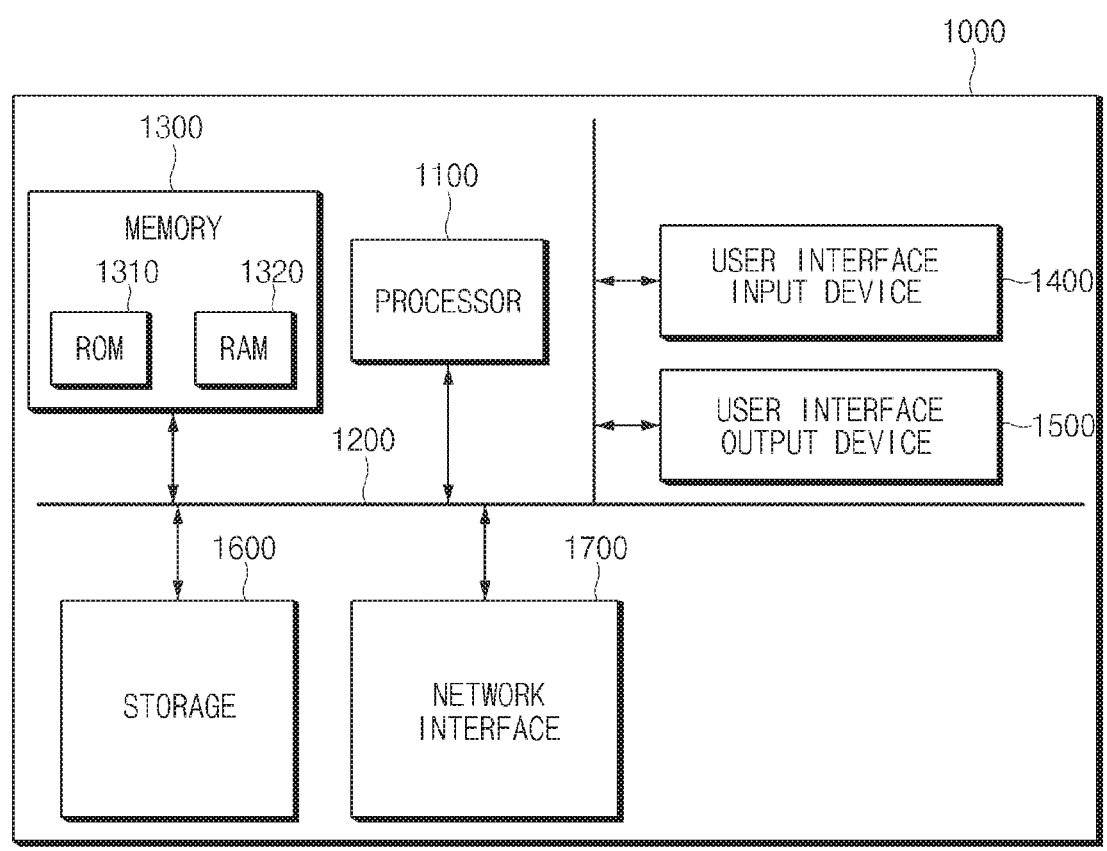
FIG. 8 is a block diagram illustrating a computing system for executing a method of operating a convenient device of a vehicle according to an exemplary embodiment of the present disclosure.

FIG. 8 is a block diagram illustrating a computing system for executing a method of operating a convenient device of a vehicle according to an exemplary embodiment of the present disclosure. Referring to FIG. 8, the method of operating a convenient device of a vehicle according to an exemplary embodiment of the disclosure may be implemented through a computing system. A computing system 1000 may include at least one processor 1100, a memory 1300, a user interface input device 1400, a user interface output device 1500, storage 1600, and a network interface 1700, which are connected with each other via a bus 1200.

The processor 1100 may be a central processor (CPU) or a semiconductor device that processes instructions stored in the memory 1300 and/or the storage 1600. The memory 1300 and the storage 1600 may include various types of volatile or non-volatile storage media. For example, the memory 1300 may include a ROM (Read Only Memory) and a RAM (Random Access Memory).

Thus, the operations of the method or the algorithm described in connection with the embodiments disclosed herein may be embodied directly in hardware or a software module executed by the processor 1100, or in a combination thereof. The software module may reside on a storage medium (that is, the memory 1300 and/or the storage 1600) such as a RAM, a flash memory, a ROM, an EPROM, an EEPROM, a register, a hard disk, a solid state drive (SSD), a removable disk, a CD-ROM. The exemplary storage medium may be coupled to the processor 1100, and the processor 1100 may read information out of the storage medium and may record information in the storage medium. Alternatively, the storage medium may be integrated with the processor 1100. The processor 1100 and the storage medium may reside in an application specific integrated circuit (ASIC). The ASIC may reside within a user terminal In another case, the processor 1100 and the storage medium may reside in the user terminal as separate components.

According to the convenient device control apparatus for a vehicle and the method thereof according to the exemplary embodiments, it may be possible to detect a user's intention to operate a convenient device based on the EEG signal of a user and operate the corresponding convenient device that corresponds to the detected intention of the user, thereby allowing the user to more easily operate various convenient devices mounted within the vehicle.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

Therefore, the exemplary embodiments of the present disclosure are provided to explain the spirit and scope of the present disclosure, but not to limit them, so that the spirit and scope of the present disclosure is not limited by the embodiments. The scope of the present disclosure should be construed on the basis of the accompanying claims, and all the technical ideas within the scope equivalent to the claims should be included in the scope of the present disclosure.

What is claimed is:

1. A convenient device control apparatus for a vehicle, comprising:
   one or more light sources configured to emit i) light of a first color and ii) light of a second color that is different than the light of the first color;
   an electroencephalogram (EEG) sensor configured to measure an EEG signal of a user staring at i) the light of the first color and ii) the light of the second color;
   a controller configured to:
   analyze a frequency of the EEG signal measured by the EEG sensor; and
   operate a convenient device in the vehicle based on the frequency of the EEG signal.

2. The convenient device control apparatus of claim 1, wherein the controller is configured to change a light emission cycle of the light source that corresponds to an operation state of the convenient device.

3. The convenient device control apparatus of claim 1, wherein the controller is configured to change a light emission color of the light source that corresponds to a light emission cycle of the light source.

4. The convenient device control apparatus of claim 1, wherein the controller is configured to operate the light source to emit light a specified number of times by a time interval at a time point when operating the convenient device.

5. The convenient device control apparatus of claim 1, wherein the controller is configured to increase a light emission intensity of the light source at a time point when operating the convenient device.

6. The convenient device control apparatus of claim 1, wherein the controller is configured to change a light emission color of the light source at a time point when operating the convenient device.

7. A method of controlling a convenient device of a vehicle, comprising:
   emitting, by a light source, light of a first color in a first cycle;
   measuring, by an electroencephalogram (EEG) sensor, an EEG signal of a user;
   analyzing, by an EEG analyzer, a frequency of the EEG signal measured by the EEG sensor; and operating, by a controller, a convenient device in the vehicle based on the frequency of the EEG signal analyzed by the EEG analyzer.

8. The method of claim 7, wherein the operating of the convenient device in the vehicle includes changing the light emission cycle of the light source that corresponds to an operation state of the convenient device.

9. The method of claim 7, wherein the operating of the convenient device in the vehicle includes changing a light emission color of the light source that corresponds to a light emission cycle of the light source.

10. The method of claim 7, wherein the operating of the convenient device in the vehicle includes allowing the light source to emit light a specified number of times by a time interval at a time point when operating the convenient device.

11. The method of claim 7, wherein the operating of the convenient device in the vehicle includes increasing a light emission intensity of the light source at a time point when operating the convenient device.

12. The method of claim 7, wherein the operating of the convenient device in the vehicle includes changing a light emission color of the light source at a time point when operating the convenient device.

13. The method of claim 7, wherein the light source is located around the convenient device.

14. A convenient device control apparatus for a vehicle, comprising:
a plurality of light sources configured to emit light of different colors at different cycle;
an electroencephalogram (EEG) sensor configured to measure an EEG signal of a user staring at the light of different colors;
a control configured to:
analyze a frequency of the EEG signal measured by the EEG sensor; and
operate a convenient device in the vehicle based on the frequency of the EEG signal analyzed by the EEG analyzer.

15. The convenient device control apparatus of claim 14, wherein the controller is configured to operate the convenient device when an EEG signal having a first frequency and an EEG signal having a second frequency are successively measured within a specified time.

16. The convenient device control apparatus of claim 14, wherein the controller is configured to change a light emission color of the light source that corresponds to the light emission cycle of the light source.

17. The convenient device control apparatus of claim 14, wherein the controller is configured to operate the light source to emit light a specified number of times by a time interval at a time point when operating the convenient device.

18. The convenient device control apparatus of claim 14, wherein the controller is configured to increase a light emission intensity of the light source at a time point when operating the convenient device.

19. The convenient device control apparatus of claim 14, wherein the controller is configured to change a light emission color of the light source at a time point when operating the convenient device.

20. The convenient device control apparatus of claim 14 wherein a first light source of the plurality of light sources emits at a first frequency and a second light source of the plurality of light sources emits a second frequency which is different than the first frequency.

* * * * *